United States Patent [19]  [11] 4,169,104
Burt et al.  [45] Sep. 25, 1979

[54] METHOD OF PREPARING SALTS OF ESTERS OF PENTAVALENT ANTIMONY

[75] Inventors: Gerald D. Burt, Shaker Heights; Anton Mudrak, Broadview Heights, both of Ohio

[73] Assignee: The Harshaw Chemical Company, Cleveland, Ohio

[21] Appl. No.: 890,347

[22] Filed: Mar. 27, 1978

Related U.S. Application Data

[63] Continuation-in-part of Ser. No. 779,191, Mar. 18, 1977, abandoned.

[51] Int. Cl.$^2$ .......... C07F 9/90; C07F 15/02; C07F 15/04; C07F 15/06
[52] U.S. Cl. .......... 260/438.1; 252/8.1; 260/439 R; 260/446
[58] Field of Search .......... 260/439 R, 438.1, 446

[56] References Cited

U.S. PATENT DOCUMENTS

| | | | |
|---|---|---|---|
| 1,990,442 | 2/1935 | Traube et al. | 260/446 |
| 2,031,268 | 2/1936 | Kussmaul | 260/446 |
| 2,066,742 | 1/1937 | Schmidt | 260/446 |
| 2,880,222 | 3/1959 | Friedheim | 260/446 |
| 3,448,046 | 6/1969 | Schalin | 260/446 X |
| 3,657,179 | 4/1972 | Yates | 260/446 X |
| 3,676,476 | 7/1972 | Randolph | 260/446 |
| 3,676,477 | 7/1972 | Chay et al. | 260/448 |
| 3,763,202 | 10/1973 | Cumbo et al. | 260/446 |
| 3,836,557 | 9/1974 | Knowles | 260/446 |

*Primary Examiner*—Helen M. S. Sneed
*Attorney, Agent, or Firm*—Armand P. Boisselle; James A. Lucas

[57] ABSTRACT

A method of preparing esters and salts of esters of pentavalent antimony from hydrated metal antimonates is disclosed. The method comprises heating a mixture of a hydrated metal antimonate and an organic compound selected from the group consisting of (i) a polyhydroxy or a polymercapto compound containing vicinal hydroxy or mercapto groups, or a mixture of the two groups,
(ii) an alpha-hydroxy or alpha-mercapto carboxylic acid or thiocarboxylic acid, and
(iii) glyoxal, to a temperature sufficient to form the salt of the ester. The salts which are prepared in this manner are effective flame retardants for cotton and other organic polymers.

12 Claims, No Drawings

METHOD OF PREPARING SALTS OF ESTERS OF PENTAVALENT ANTIMONY

CROSS-REFERENCE TO RELATED APPLICATION

This application is a continuation-in-part of our pending application Ser. No. 779,191 filed Mar. 18, 1977, now abandoned.

BACKGROUND OF THE INVENTION

This invention relates to a method of preparing esters of pentavalent antimony, and more particularly, to a method of preparing metal salts of such esters from hydrated metal antimonates. The invention also relates to certain metal salts which are novel.

Various antimony compounds have been used as flame retardants for organic polymers and plastics. A commonly used compound is antimony trioxide, but its applications are limited because it is insoluble in water and other common solvents. Because of this insolubility, antimony trioxide is difficult to introduce within fibers and plastics. When applied to the outside of fibers and fabrics, the antimony trioxide is subject to mechanical wear and abrasion and is readily lost from the surface unless special binders are used. The use of binders, however, increases the stiffness of the fabrics and fibers further reducing the suitability of antimony trioxide as a flame retardant.

Glycerine and glycol esters of trivalent antimony are also known and have been suggested as being useful as flame retardants. However, these trivalent antimony esters generally are not soluble in polar organic solvents commonly used to dissolve polymers for spinning, and therefore cannot conveniently be incorporated into films or fibers of the polymers. Esters of pentavalent antimony have been prepared and these are soluble in polar solvents. Accordingly, they are well suited for processing organic polymers and can be conveniently incorporated into the polymers. Some of the esters are, however, highly sensitive to moisture. The salts of the esters are reported to be more resistant to moisture in U.S. Pat. No. 3,836,557.

A number of procedures for preparing esters of pentavalent antimony which are useful as flame retardants have been suggested in the art. In U.S. Pat. No. 3,873,451, a group of esters derived, at least in part from aliphatic polyhydroxy compounds having 2 to 6 carbon atoms and vicinal hydroxy groups are described. The esters are made by oxidizing antimony trihalide with nitric acid to form a hydrated oxide of pentavalent antimony which is reacted with an aliphatic polyhydroxy compound containing 2 to 6 carbon atoms and a vicinal hydroxyl group. A variety of water-soluble salts of pentavalent antimony glycol esters are described in U.S. Pat. No. 3,836,557 as being useful flame retardants for materials such as textiles or polymeric resins. A typical salt is tri(ethylenedioxy) hydrogen antimony (V), sodium salt. In addition to the metal salts, the patent describes guanidinium, ethylenediammonium and ammonium type salts of the esters and their use as flame retardants.

U.S. Pat. No. 3,657,179 describes antimony esters which are derived, at least in part, from alpha-hydroxy carboxylic acids. Such esters also are readily soluble in polar organic solvents and can be combined with spinning or casting solutions of organic polymers. The spun or cast polymer articles obtained from such solutions contain the dispersed antimony compound and are resistant to combustion.

SUMMARY OF THE INVENTION

This invention relates to a simplified process for the production of esters of pentavalent antimony and salts of such esters and to the esters and salts obtained by the process. The method of this invention for preparing the salts of the esters of pentavalent antimony comprises the steps of (a) preparing a mixture of a hydrated metal antimonate and an organic compound selected from the group consisting of
(i) a polyhydroxy or a polymercapto compound containing vicinal hydroxy or mercapto groups, or a mixture of the two groups,
(ii) an alpha-hydroxy or alpha-mercapto carboxylic or thiocarboxylic acid, and
(iii) glyoxal, and (b) heating the mixture to a temperature sufficient to form the ester. The formation of the esters of pentavalent antimony of the above process proceeds without complication and does not require any special equipment. The esters of pentavalent antimony which are prepared in accordance with the method of the invention are useful as smoke suppressants and flame retardants in textiles and polymeric compositions.

DESCRIPTION OF THE PREFERRED EMBODIMENTS

The esters of pentavalent antimony are obtained in accordance with the method of the invention by heating a mixture of a hydrated metal antimonate and an organic compound which may be (i) a polyhydroxy or a polymercapto compound containing vicinal hydroxy or mercapto groups, or a mixture of these two groups,
(ii) an alpha-hydroxy or alpha-mercapto carboxylic acid or thiocarboxylic acid, and
(iii) glyoxal, to an elevated temperature which is sufficient to produce the antimony esters.

The metal antimonates which are useful in the method of the invention are the hydrated metal antimonates having the following general formula $$M[Sb(OH)_6]_x \qquad \text{FORMULA I}$$

wherein M represents a metal such as sodium, potassium, magnesium, calcium, barium, strontium, zinc, cadmium, copper, iron, cobalt, nickel, etc., and x is an integer equal to the valence of the metal. Accordingly, x equals 1 for sodium and potassium, 2 for calcium and barium, etc. Generally, M is an alkali or alkaline earth metal, zinc, copper, iron, cobalt or nickel.

Hydrated metal antimonates are known and are commercially available. They have been produced by a variety of methods. Alkali metal antimonates have been made by fusing antimony, antimony oxide or antimony sulfide with an alkali-metal hydroxide with sodium or potassium nitrate, and thereafter separating the antimonate from the other reaction products by extraction. The preparation of hydrated potassium antimonate by oxidation of a slurry of antimony trioxide in a potassium hydroxide solution is described in U.S. Pat. No. 2,926,994. Hydrogen peroxide is used as an oxidizing agent. The potassium antimonate which is soluble in water can be converted to other hydrated metal antimonates which are insoluble by the addition of metal salts such as sulfates which form insoluble antimonates. Examples of hydrated antimonates which can be prepared in this manner include sodium antimonate, barium antimonate, calcium antimonate, copper antimonate, nickel antimonate, iron antimonate, cobalt antimonate, zinc antimonate, etc. The source of the hydrated metal antimonate utilized in the method of the invention is not critical.

The polyhydroxy compounds containing vicinal hydroxy groups which are useful in the method of the invention generally will contain from about 2 to 6 carbon atoms. They may be represented by the formula

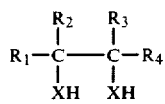

FORMULA II wherein $R_1$, $R_2$, $R_3$ and $R_4$ are each independently hydrogen, alkyl groups of from 1 to about 4 carbon atoms, hydroxyalkyl or mercaptoalkyl groups of from 1 to 4 carbon atoms and wherein each X is independently oxygen or sulfur. Preferably, the total number of carbon atoms in $R_1$, $R_2$, $R_3$ and $R_4$ does not exceed 4.

Examples of suitable polyhydroxy compounds include ethylene glycol; glycerol; 1,2-propanediol; 1,2-butanediol; 1,2-pentanediol; 2,3-pentanediol; 1,2-hexanediol; 2,3-hexanediol; etc.

Dimercaptoethane is an example of a useful polymercapto compound. Examples of compounds containing a mixture of hydroxy and mercapto groups which also are useful in the method of the invention include mercaptoethanol; 1,3-dimercapto-2-propanol; 2,3-dimercapto-1-propanol; 3-mercapto-1,2-propanediol; 1,4-dimercapto-2,3-butanediol, etc.

The alpha-hydroxy and alpha-mercapto carboxylic or thiocarboxylic acids useful in the method of this invention are aliphatic carboxylic and thiocarboxylic acids containing from 2 to 6 carbon atoms and having a hydroxy group or a mercapto group attached to the carbon chain at a position which is alpha to the carbonyl groups. As used in this application, the term alpha-hydroxy carboxylic acid includes oxalic acid in which the hydroxyl group is part of the second carboxyl group of the dicarboxylic acid. The thiocarboxylic acids corresponding to the above carboxylic acids also are useful as organic compounds for reaction with the metal antimonates in accordance with the process of the invention.

The acids may contain more than one carboxyl group as in the case of oxalic acid or more than one thiocarboxyl group, and may contain also more than one alpha-hydroxy carboxylic acid grouping, such as, for example, tartaric acid and citric acid. Other examples of suitable alpha-hydroxy carboxylic acids useful of the method of the invention include in addition to those named above, malic acid, hydroxyacetic acid, mucic acid, lactic acid, glyceric acid, gluconic acid, etc. Examples of alpha-mercapto carboxylic acids useful in the method of the invention include thiolactic, thiomalic acid, thioglycolic acid, 2-mercapto propionic acid, etc. The corresponding mercapto and hydroxy substituted thiocarboxylic acids also are useful in the method of the invention.

Glyoxal also can be reacted with hydrated metal antimonates to form metal salts of antimony esters. The glyoxal is introduced into the reaction mixture as an aqueous solution.

The reaction between the hydrated metal antimonates and the organic compounds described above generally is conducted in the presence of an excess of the organic compound which serves as a solvent or dispersing medium for the reaction mixture and/or the product of the reaction. Thus, in order to prepare the triesters of pentavalent antimony, the reaction medium will contain at least 6 moles of the above described reactive compounds per atom of antimony present in the antimonate. For example, at least 6 moles of ethylene glycol will be present for the reaction with hydrated sodium antimonate and at least 12 moles of ethylene glycol will be available for reaction with 1 mole of hydrated calcium antimonate. In some instances other liquid media such as water also may be present as the dispersing medium or part of the dispersing medium. However, the water should not be present in amounts which would interfere with the esterification reaction or adversely react with the product of the reaction.

The reaction between the hydrated metal antimonates and the above-identified organic compounds is effected by heating the mixture to an elevated temperature whereupon the ester is formed. In general, temperatures of from about 95° to about 175° C. are utilized.

The metal salts obtained by the method of the invention may be characterized by the formula

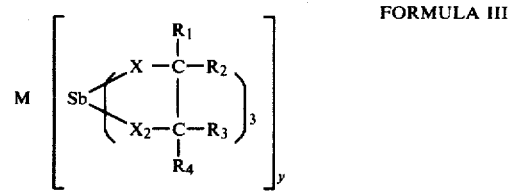

FORMULA III wherein M is a metal such as an alkali or alkaline earth metal, zinc, cobalt, copper, nickel or iron, X and $X_2$ are each independently O or S, $R_1$, $R_2$, $R_3$ and $R_4$ are each independently hydrogen, alkyl, hydroxyalkyl, mercaptoalkyl, and two of the R groups on a carbon atom taken together may be =O, and y is equal to the valence of the metal M.

The following examples illustrate the method of the invention for preparing metal salts of triesters of pentavalent antimony. Unless otherwise indicated, all parts and percentages are by weight.

EXAMPLE 1

A mixture of 20 grams of hydrated sodium antimonate in 200 ml. of ethylene glycol is heated to about 140°-150° C. and maintained at this temperature for three hours. After two hours, the sodium antimonate appears to be dissolving, and after three hours a clear, but dark brown solution is observed. The mixture is heated an additional 0.5 hour and filtered to remove a slight haze. The filtrate is allowed to cool to room temperature whereupon a mass of white granules crystallizes from the brown filtrate. These white crystals are removed by filtration, press dried, washed three times with acetone and oven dried at 60° C. for one hour. The crystals have a melting point of from 134°-135° C. An analysis of the crystals indicated the product to be tri- (ethylenedioxy) hydrogen antimony (V), sodium salt solvated with 3 moles of ethylene glycol.

| Analysis: | Calculated | Found |
|---|---|---|
| %Sb = | 23.8 | 23.8 |
| %Na = | 4.50 | 4.24 |

EXAMPLE 2

The procedure of Example 1 is repeated except that the sodium antimonate is replaced by an equivalent amount of hydrated potassium antimonate which produces the potassium salt of tri(ethylenedioxy) hydrogen antimony (V).

EXAMPLE 3

A mixture of 37 grams of hydrated sodium antimonate and 200 ml. of glycerol is stirred at 140°–160° C. for three hours. The mixture is filtered and allowed to cool. Acetone is added to the cooled filtrate to precipitate the desired sodium salt of the triester which is hygroscopic but stable in water solution at room temperature for one day.

EXAMPLE 4

A stirred solution of 130 grams of glyoxal (30%) in 100 ml. of water is prepared, and hydrated sodium antimonate is added in portions until no more can be dissolved in the solution. Approximately 29 grams of the antimonate are added to the mixture while the mixture is maintained at a temperature of 90° C.

The mixture is filtered and concentrated to about 200 ml. After cooling at room temperature, about 400 ml. of acetone is added. The desired glyoxal triester is precipitated as hygroscopic amorphous product.

EXAMPLE 5

A mixture of 30 grams of hydrated sodium antimonate in 175 ml. of propylene glycol is stirred at 140°–160° C. for four hours. The mixture is filtered while hot, and the filtrate is cooled. Diethyl ether is added to slowly precipitate the desired triester which is washed with acetone and analyzed. The solid sodium salt of the triester obtained in this manner has a softening point of about 148°–150° C. The chemical analysis of the product indicates the desired triester is solvated with two moles of water.

| Analysis: | Calculated | Found |
|---|---|---|
| %Sb = | 30.23 | 30.5 |
| %Na = | 5.7 | 5.3 |

EXAMPLE 6

A mixture of 26 parts of hydrated sodium antimonate, 46 parts of glycolic acid (hydroxy acetic acid) and 200 parts of water is heated to about 100° C. and all of the solids are dissolved within 0.5 hour. The solution is filtered while hot, and an excess of acetone is added to precipitate the desired product.

EXAMPLE 7

The procedure of Example 6 is repeated except that the glycolic acid is replaced by an equivalent amount of thioglycolic acid.

EXAMPLE 8

The procedure of Example 6 is repeated except that the glycolic acid is replaced by an equivalent amount of lactic acid.

EXAMPLE 9

The procedure of Example 6 is repeated except that the glycolic acid is replaced by an equivalent amount of thiomalic acid.

EXAMPLE 10

The procedure of Example 6 is repeated except that the glycolic acid is replaced by an equivalent amount of gluconic acid.

EXAMPLE 11

The mixture of 100 grams of 2,3-dihydroxybutane and 10 grams of hydrated sodium antimonate is stirred at 150°–165° C. for a total of 16 hours. At this time, most of the sodium antimonate is reacted and dissolved. The reaction mixture is filtered while hot and the filtrate solidifies almost immediately. The solid mass obtained in this manner is dried and washed with acetone. (Some of the solids dissolve in the acetone but may be recovered.) The crystals obtained in this manner, recrystallized from acetonitrile melt at 109°–110° C., and a chemical analysis of the product indicates the desired triester is solvated with 2.5 moles of the butanediol.

| Analysis: | Calculated | Found |
|---|---|---|
| %Sb = | 19.2 | 19.7 |
| %Na = | 3.6 | 3.5 |

EXAMPLE 12

The procedure of Example 1 is followed except that the sodium antimonate is replaced by an equivalent amount of copper (2) antimonate, and the mixture is heated at 150°–160° C. for about 5 hours. After the unreacted material is removed by filtration, the filtrate is cooled overnight to −5° C. The resulting light blue product crystals are washed with acetone and have a melting point of about 196°–197° C. Analysis of the product indicates the desired triester is solvated with five moles of ethylene glycol.

| Analysis: | Calculated | Found |
|---|---|---|
| %Cu = | 6.5 | 6.5 |
| %Sb = | 24.9 | 25.2 |

EXAMPLE 13

The procedure of Example 12 is repeated except that an equivalent amount of cobalt (2) antimonate is used in lieu of the copper antimonate. The product crystals are light pink and have a melting point of about 197°–200° C. Analysis of the product indicates the desired triester is solvated with five moles of ethylene glycol.

| Analysis: | | |
|---|---|---|
| | Calculated | Found |
| %Co = | 6.0 | 6.2 |
| %Sb = | 25.0 | 25.1 |

EXAMPLE 14

The procedure of Example 12 is repeated except that zinc antimonate is used in lieu of the copper antimonate. The zinc antimonate is prepared by addition of an aqueous solution of potassium antimonate to a sufficient amount of a 30% aqueous solution of zinc sulfate at about 60° C. Although the zinc antimonate begins to precipitate immediately, the reaction mixture is stirred for about one hour to ensure completion of the reaction. The precipitate is reslurried in water, filtered and dried. The reaction of the zinc antimonate with the ethylene glycol results in the formation of white crystals having a melting point of 193°–195° C. Analysis of the product indicates the triester is solvated with 5 moles of ethylene glycol.

| Analysis: | | |
|---|---|---|
| | Calculated | Found |
| %Zn = | 6.68 | 6.8 |
| %Sb = | 24.9 | 25.4 |

EXAMPLE 15

The procedure of Example 12 is repeated utilizing nickel antimonate prepared from potassium antimonate and nickel sulfate by the procedure described in Example 14. The product obtained by reaction of the nickel antimonate with ethylene glycol are light aqua crystals having a melting point of 220°–222° C. Analysis indicates the desired triester is solvated with five moles of ethylene glycol.

| Analysis: | | |
|---|---|---|
| | Calculated | Found |
| %Ni = | 6.4 | 6.4 |
| %Sb = | 25.0 | 25.9 |

EXAMPLE 16

The procedure of Example 12 is repeated except that iron (2) antimonate is used in lieu of the zinc antimonate. The iron (2) antimonate is prepared by reaction of potassium antimonate with iron sulfate by the procedure described in Example 14. The product crystals obtained by reacting the iron antimonate with ethylene glycol are light yellow with a melting point of 183°–186° C. Analysis indicates the desired triester is solvated with five moles of ethylene glycol.

| Analysis: | | |
|---|---|---|
| | Calculated | Found |
| %Fe = | 5.8 | 6.4 |
| %Sb = | 25.1 | 25.9 |

The compounds of the invention are soluble and stable in methanol, and may be recrystallized from various methanol-hydrocarbon mixtures such as methanol-benzene, methanol-hexane, etc. The salts are useful as smoke suppressants in plastics, particularly the nickel and iron salts. The salts are effective flame retardants in textiles and various polymeric compounds.

The embodiments of the invention in which an exclusive property or privilege is claimed are defined as follows:

1. A method of preparing esters of pentavalent antimony which comprises the steps of
    (a) preparing a mixture of a hydrated metal antimonate and an organic compound selected from the group consisting of
        (i) a polyhydroxy or a polymercapto compound containing vicinal hydroxy or mercapto groups, or a mixture of the two groups,
        (ii) An alpha-hydroxy or alpha-mercapto carboxylic or thiocarboxylic acid, and
        (iii) glyoxal, and
    (b) heating the mixture to a temperature sufficient to form the ester.
2. The method of claim 1 wherein the organic compound in the mixture contains from 2 to about 6 carbon atoms.
3. The method of claim 1 wherein the metal antimonate is a hydrated alkali metal antimonate.
4. The method of claim 1 wherein the organic compound is a polyhydroxy compound containing vicinal hydroxy groups and from 2 to about 6 carbon atoms.
5. The method of claim 1 wherein the organic compound is an alpha-hydroxy carboxylic acid containing from 2 to about 6 carbon atoms.
6. The method of claim 1 wherein the mixture also contains water.
7. The method of claim 1 wherein the molar ratio of organic compound to metal antimonate in the mixture is at least 3:1.
8. The method of claim 4 wherein the polyhydroxy compound is ethylene glycol.
9. The method of claim 2 wherein the metal antimonate is sodium antimonate and the organic compound is ethylene glycol.
10. Metal salts of antimony esters having the formula

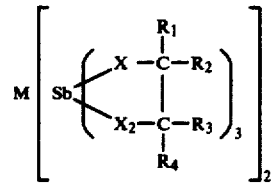

wherein M is copper, nickel, iron or cobalt,
X and $X_2$ are each independently O or S, and
$R_1$, $R_2$, $R_3$ and $R_4$ are each independently hydrogen, alkyl, hydroxy-alkyl, mercaptoalkyl or two of the R groups taken together may be =O.
11. Metallic salts of claim 10 having the formula

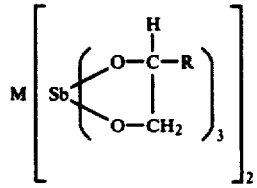

wherein M is copper, nickel, iron or cobalt, and R is hydrogen, methyl or hydroxymethyl.
12. The salts of claim 11 wherein R is hydrogen.